United States Patent [19]

Kaiser

[11] 4,217,279

[45] Aug. 12, 1980

[54] SYNTHESIS OF STEROIDS

[76] Inventor: Emil T. Kaiser, 5634 S. Woodlawn Ave., Chicago, Ill. 60639

[21] Appl. No.: 970,471

[22] Filed: Dec. 18, 1978

[51] Int. Cl.² ........................... C07J 9/00; C07J 71/00
[52] U.S. Cl. ........................ 260/239.55 R; 260/397.1; 260/397.5; 260/397.2
[58] Field of Search ............... 260/397.1, 397.2, 397.3, 260/397.5

[56] References Cited

U.S. PATENT DOCUMENTS

| | | | |
|---|---|---|---|
| 3,882,254 | 7/1974 | Partridge, Jr. et al. | 260/397.2 |
| 3,887,545 | 6/1975 | Iacobelli | 260/397.2 |
| 4,134,904 | 1/1979 | Kaiser | 260/397.1 |

Primary Examiner—Elbert L. Roberts

[57] ABSTRACT

The synthesis of 25-hydroxycholesterol and 1α,25-dihydroxycholesterol in which the sterol nucleus of an ester of hyodeoxycholic acid is stabilized by protection of the 3 and 6α-hydroxyl groups with alkyl groups, alkyl ether groups, preferably with the 3β-methoxyethoxymethyl group or with the heterocyclic 2-tetrahydropyran group, then extending the chain from the carbon at the 24-position to a cyanide group at the 25-position and then subjecting the sterol so formed to a series of reactions by which it is transformed into 1α,25-dihydroxycholesterol or by a modified series of reactions to 25-hydroxycholesterol.

26 Claims, No Drawings

SYNTHESIS OF STEROIDS

This invention relates to synthesis of steroids and more particularly to the synthesis of 1α,25-dihydroxycholesterol and to processes and intermediates for the preparation thereof.

BACKGROUND

The hydroxylated vitamin $D_3$ derivatives, 25-hydroxycholecalciferol and 1α,25-dihydroxycholesterol can be prepared from 25-hydroxycholesterol and 1α,25-dihydroxycholesterol. The synthesis of these hydroxylated cholesterols from the hog bile constituent, hyodeoxycholic acid, has been described by me in applications, Ser. No. 816,478, 829,009, 876,753 and 929,932. In the applications serial numbers 816,478, 829,009 and 929,932 I describe the synthesis of 25-hydroxycholesterol from hyodeoxycholic acid esters, and in application serial number 876,753 I describe the synthesis of a 25-hydroxylated cholestane derivative, 25-hydroxy-5β-cholestan-3,6-dione, from hyodeoxycholic acid esters. This compound is an intermediate in the synthesis of 1α,25-dihydroxycholesterol, as shown by T. A. Narwid, J. F. Blount, J. A. Iacobelli and M. R. Uskokovic, Helv. Chim. Acta, 57, 781 (1974).

An object of the present invention is to seek new processes and steroids which can serve as intermediates in the synthesis of 25-hydroxycholesterol and 1α,25-dihydroxycholesterol. Such new intermediates and processes increase the options for synthesis and constitute improvements in the production of hydroxylated cholesterols.

SUMMARY

In the synthesis of new steroids from 3α-hydroxy-5-cholenic acid and esters thereof, the 3α-hydroxyl may be protected as disclosed in my application Ser. No. 816,478. I have now found that both the 3α- and the 6α-hydroxyl of hyodeoxycholic acid and esters thereof can be protected against the subsequent action of reagents used for the extension of the hyodeoxycholic acid side chain by one carbon. The 3α- and 6α-hydroxyls are protected by alkyl groups, alkyl ether groups, such as the β-methoxyethoxymethyl group, or by the tetrahydropyranyl group, all of which stabilize the steroid nucleus against the further reactions needed to form the desired steroids.

DISCLOSURE OF THE INVENTION

The new synthesis may start with an ester of hyodeoxycholic acid obtained from animal bile. This ester may be any aliphatic or cyclic ester of this bile acid, but I prefer the methyl ester since it may be obtained directly from bile acid hydrolyzates. This ester may be described by the following structural formula.

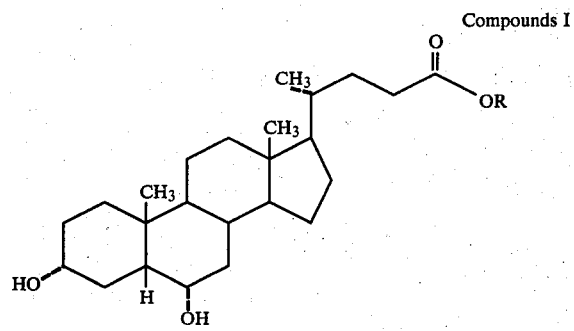

Compounds I where R is an aliphatic or cyclic group, preferably methyl.

In the next step of the synthesis, protecting groups are placed on the 3α- and 6α-hydroxyls of Compound I. These protecting groups have to remain stable against the action of alkaline reducing agents to be used in the subsequent steps of the synthesis. Alkyl protecting groups are suitable for this purpose. Alkyl ethers are formed by the reaction of alkyl halides with sodium alcoholates. They do not react with sodium and are unchanged by treatment at moderate temperatures with strong acids or bases. They can be split fairly easily by halogen acids, particularly hydrogen iodide.

Other suitable protecting groups are alkyl ether groups capable of ether bond formation. Alkyl ether groups can be removed under mild conditions. Tertiary butoxycarbonyl or tertiary amyloxycarbonyl groups are decomposed by dilute acids at room temperature, leading to the restoration of the hydroxyl groups. β-Methoxyethoxymethoxy (MEM) ethers are cleaved by Lewis acids, such as zinc bromide, at room temperature, yielding free alcohols.

To prepare the MEM ether compound, Compound I may be dissolved in methylene chloride. MEM-chloride and a tertiary amine may be added, and the mixture agitated for several hours, for example 5 hours, at room temperature until the reaction is completed. From the solution, the di-MEM ether of Compound I is isolated.

In another preferred procedure Compound I may be mixed with dihydropyran and p-toluenesulfonic acid in dioxane solution and agitated at room temperature for a longer period of time, e.g., overnight. After completion of the reaction the di-2-tetrahydropyranyl (THP) ether of Compound I is isolated. The protected derivatives of Compound I are herein called Compound II, having the following structural formula.

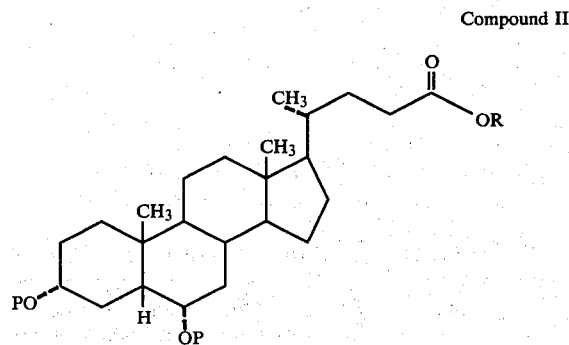

Compound II where R is an alkyl or cyclic group and P is alkyl, alkyl ether, preferably β-methoxyethoxymethyl, or 2-tetrahydropyranyl.

Since the 6α-hydroxyl group is vulnerable to elimination with the formation of a 5,6-double bond as shown by P. Ziegler and S. D. Hochner, U.S. Pat. No. 2,781,364 (1957), and either the 2-tetrahydropyranyl or the β-methoxyethoxymethyl groups may be removed under mild reaction conditions, the use of the protective groups at the 6α-position is of special importance.

Compound II may be reduced by a reducing agent to transform the 24-carboxylic ester group into a 24-hydroxyl group, without having the protecting groups on the 3α and 6α-hydroxyls affected during the course of the reaction. Since the preferred protecting groups MEM and THP are sensitive to acid but stable under alkaline conditions, alkaline reducing agents may be used. Such reagents are, for example, sodium or sodium anilidoborohydride which reduce carboxylic acids and esters thereof to alcohols.

Reducing agents of preference are sodium, potassium or lithium complexes of aluminum hydride, which by heating Compound II in toluene solution to, for example 80° C., for two hours, reduce the 24-carboxylic ester to a 24-alcohol to produce Compound III, having the structure:

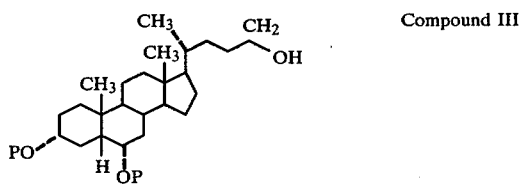

Compound III where P is alkyl, alkyl ether, preferentially β-methoxyethoxymethyl or 2-tetrahydropyranyl.

Compound III may be mixed in pyridine solution with an aromatic sulfonyl halide, for example, p-toluenesulfonyl chloride, benzenesulfonyl bromide, naphthylsulfonyl chloride or with an alkylsulfonyl chloride, for example, methanesulfonyl chloride, ethanesulfonyl bromide, p-toluenesulfonyl chloride being the sulfonyl reagent of preference, to obtain the compound herein designated Compound IV, having the structure:

Compound IV

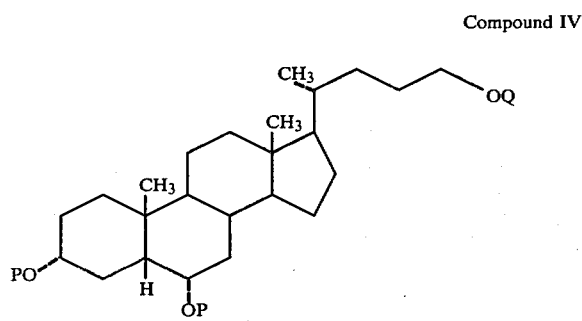

where P is alkyl, alkyl ether, preferentially β-methoxyethoxymethyl or 2-tetrahydropyranyl and Q is an aromatic or alkyl sulfonyl group.

Compound IV may be treated in one embodiment of the process with potassium cyanide in dimethylformamide solution, or in another embodiment with sodium cyanide in ethanol solution for a period, such as about 20 hr., and at elevated temperatures, such as about 80°

C. The resulting 25-carbon steroid derivative is herein designated as Compound V, having the structure:

Compound V

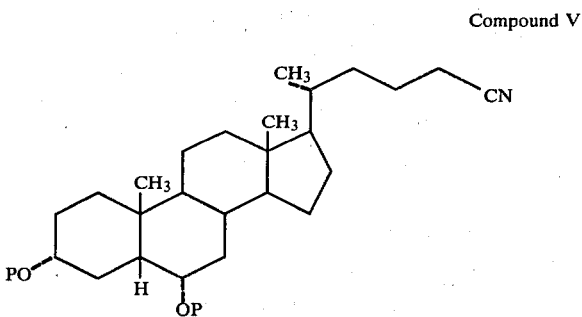

where P is alkyl, alkyl ether, preferentially β-methoxyethoxymethyl or 2-tetrahydropyranyl.

When the protecting groups of Compound V are 2-tetrahydropyranyl, they may be removed by heating in aqueous alcohol solution with p-toluenesulfonic acid. When P is β-methoxyethoxymethyl, Compound V may be stirred with zinc bromide in a solvent consisting of methylene chloride to which less than 0.1 to 5% of a lower alkyl alcohol is added, the alcohol having one to six carbons. In either case, the resultant compound is 3α,6α-dihydryoxy-25-cyano-5β-cholane, herein designated Compound VI and having the structure:

Compound VI

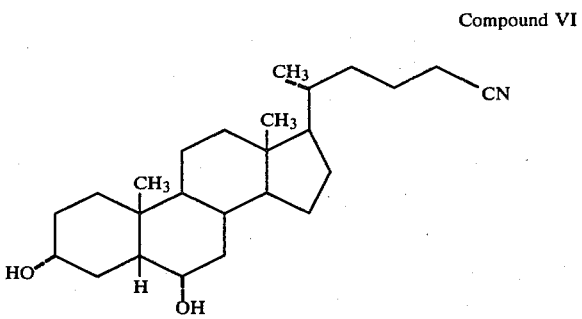

Compound VI may be saponified in aqueous alcohol with hydroxide, the solution acidified, to obtain 3α,6α-dihydroxy-5β-homocholanic acid, herein designated Compound VII, having the structure:

Compound VII

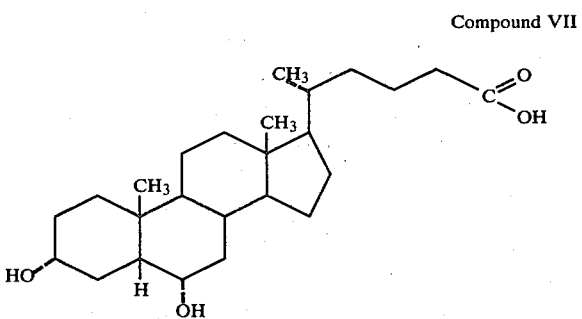

Compound VII may be dissolved in a lower alkyl alcohol containing one to nine carbons, p-toluenesulfonic acid added, and refluxed for an extended period of time, for example, 24 hrs, to yield a 3α,6α-dihydroxy-5β-homocholanic acid ester, preferably the methyl ester, herein designated Compound VIII, having the structure:

Compound VIII

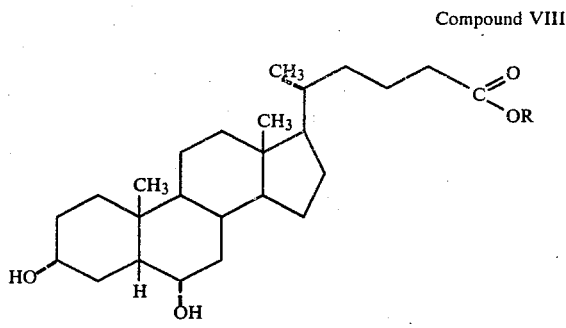

where R is a lower alkyl group containing one to nine carbons.

Compound VIII can be utilized in a variety of ways in the synthesis of hydroxylated cholesterols as illustrated by following synthetic pathways.

According to one of the pathways Compound VIII may be mixed at room temperature in pyridine solution with p-toluenesulfonyl chloride and the mixture stored at lower temperatures and for longer periods of time, for example, for 24 hr at 3° C. From this mixture an ester, preferably the methyl ester of 3α,6α-di-p-toluenesulfonyloxy-5β-homocholanic acid, may be isolated, herein designated Compound IX, having the structure:

Compound IX

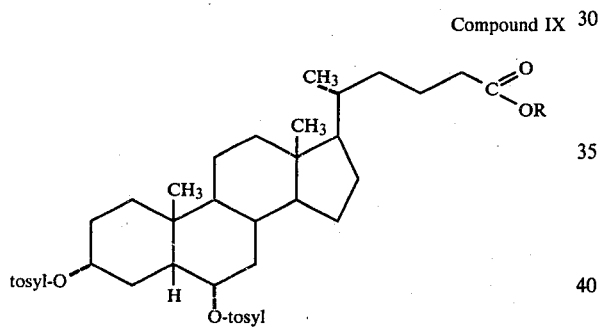

where R is a lower alkyl group having one to nine carbons.

Compound IX may be dissolved in dimethylformamide, potassium acetate in aqueous solution is added, and the mixture heated to 90° C. to 110° C. for several hours, for example 5 hrs. From the mixture a compound may be isolated, herein designated Compound X, having the structure:

Compound X

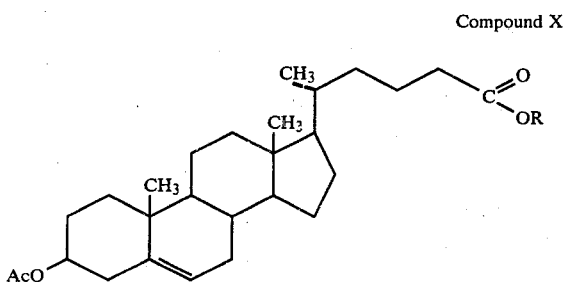

where R is a lower alkyl group having one to nine carbons.

Compound X has been described by J. C. Babcock and J. A. Campbell in U.S. Pat. No. 3,833,622 (1974). According to Example 4 of Babcock, a conjugated 7,8-double bond may be introduced into Compound X, which, in this Example, is called 3β-hydroxy-25-homochol-5-enate, 3-acetate, and designated Compound VII by Babcock. The resulting methyl 3β-hydroxy-25-homochol-5,7-dienate 3-acetate is disclosed to be transformed by several synthetic steps and by irradiation into 25-hydroxycholecalciferol.

It is a substanial advantage that in my invention compound X may be produced from an available raw material, hog bile, while Babcock obtains this compound from a minor oxidation product of cholesterol, which is difficult to prepare and in short supply.

Compound X, according to the process of my invention, may be dissolved in tetrahydrofuran, methyl magnesium bromide in tetrahydrofuran solution added, and the mixture stirred for a prolonged period, for example 24 hours. From the reaction mixture 25-hydroxycholesterol, herein designated Compound XI, may be isolated, having the structure:

Compound XI

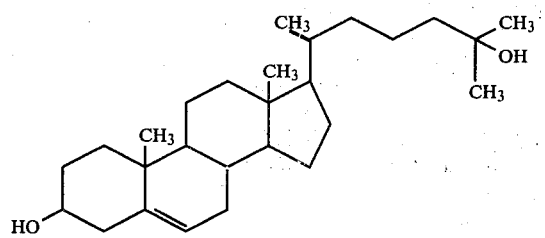

Compound XI may be transformed by an 8 step process into 1,25-dihydroxycholecalciferol according to D. H. R. Barton, R. H. Hesse, M. M. Pechet and E. Rizzardo, J.C.S. Chem. Commun., 203, 1974.

In another sequence of reactions Compound VIII may be dissolved in tetrahydrofuran and the solution added dropwise to a solution of methyl magnesium bromide in tetrahydrofuran. The mixture may be stirred at room temperature for a longer period, for example 24 hours, and magnesium complex decomposed with aqueous ammonium chloride and 3α,6α-dihydroxy-5β-chloestane isolated, herein designated as Compound XII, having the structure:

Compound XII

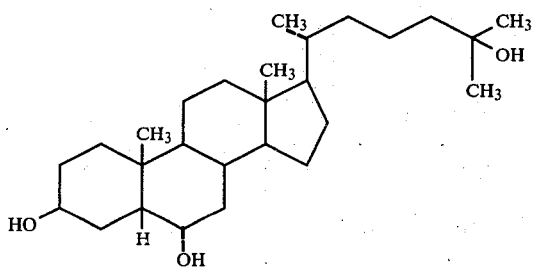

Compound XII may be dissolved in toluene, and after the addition of cyclohexanone and aluminum isopropoxide, the solution may be refluxed for 1 to 2 hours. After the solvents are evaporated from the residue, 25-hydroxy-5α-cholestan-3,6-dione is isolated. This is a compound described by T. A. Narwid, J. F. Blount, J. A. Iacobelli and M. R. Uskokovic in Helv. Chim. Acta, 57, 781 (1974). These authors converted 25-hydroxy- 5α-cholestane-3,6-dione into 1α,25-dihydroxycholesterol, used for the production of 1α,25-dihydroxycholecalciferol.

Specific examples for carrying out my improved synthesis are given as follows:

EXAMPLE 1

Methyl 3α,6α-Di(2-tetrahydropyranyloxy)-5β-cholanate (II)

To a solution of 100.0 g (0.2557 mole) of methyl hyodeoxycholate and 5.68 g of p-toluenesulfonic acid in 2000 ml of p-dioxane was added 153.7 g (1.62 mole, 148.6 ml) of dihydropyran over a period of 30 min under argon atmosphere. After stirring overnight at room temperature, the pH of the solution was adjusted to approximately pH 8 by the addition of 55 ml of 50/50 methanol/29% ammonium hydroxide. The solution was concentrated to a yellow oil under reduced pressure and the residue stirred in heptane 4 hr, then filtered to remove the precipitated p-toluenesulfonic acid. The filtrate was heated with charcoal, filtered, and evaporated to yield 116.8 g (80%) of the di-tetrahydropyranyl ether as a colorless viscous oil.

NMR (CDCl$_3$): δ4.50–4.80 (br m, 2H, methine flanked by two oxygens), 3.30–4.15 (br m, 6H, adjacent to oxygen), 3.63 (s, 3H, —OCH$_3$), 0.88 (s, 3H, C-19 —CH$_3$), 0.63 (s, 3H, C-18 —CH$_3$).

IR (CHCl$_3$): 2950, 2890, 1740, 1460, 1380, 1030 cm$^{-1}$.

Elemental Analysis: C$_{35}$H$_{58}$O$_6$: Theory %C 73.13; %H 10.17, %O 16.70. Found: %C 73.36, %H 10.02; %O 16.76.

EXAMPLE 2

3α,6α-Di(2-tetrahydropyranyloxy)-24-hydroxy-5βcholane (III)

To an 80° C. solution of 56 ml (0.202 mole) of Vitride T reagent [sodium bis(2-methoxyethoxy)aluminum hydride] in 500 ml dry toluene under argon atmosphere was added dropwise a solution of 44 g (0.0765 mole) of methyl 3α,6α-di(2-tetrahydropyranyloxy)-5β-cholanate in 75 ml dry toluene. After an additional hr at 80° C. the yellow solution was allowed to cool at room temperature, then added dropwise to 400 ml of 20% NaOH over a period of one hr with the temperature maintained below 20° C.

After stirring an additional hr, the layers were separated and the aqueous layer washed with 3×100 ml of toluene. The organic layers were combined, dried (MgSO$_4$) and concentrated under reduced pressure resulting in a yellow oil which was heated in heptane, treated with charcoal, filtered, and concentrated to yield 40.72 g (97%) of the alcohol as a colorless oil.

NMR (CDCl$_3$): δ4.45–4.75 (br m, 2H, methine flaked by two oxygens), 3.20–4.10 (br m, 9H adjacent to oxygen), 0.88 (s, 3H, C-19 —CH$_3$), 0.62 (s, 3H, C-18 —CH$_3$).

IR (CHCl$_3$): 3500, 2950, 2890, 1460, 1360, 1030 cm$^{-1}$.

EXAMPLE 3

3α,6α-di(2-tetrahydropyranyloxy)-24-p-toluenesulfonoxy-5β-cholane (IV)

To a solution of 7.10 g (0.013 mole) of the alcohol III in 200 ml of dry pyridine was added 4.19 g (0.022 mole) of p-toluenesulfonyl chloride at room temperature. The reaction mixture was chilled at 3° C. for 23 hr, then poured into 200 ml of ice water with stirring. The resulting two phase mixture was extracted with warm heptane (4×30 ml), the heptane portion dried (MgSO$_4$), heated with charcoal, filtered and concentrated under reduced pressure. The resulting colorless viscous oil totalled 7.05 g (77%).

NMR (CDCl$_3$): δ7.10–7.80 (ABq, 4H, aromatic), 4.50–4.75 (br m, 2H, methine flanked by two oxygens), 3.20–4.10 (br m, 8H adjacent to oxygen), 2.42 (s, 3H Ar-CH$_3$), 0.88 (s, 3H, C-19 —CH$_3$), 0.57 (s, 3H, C-18 —CH$_3$).

IR (CHCl$_3$): 2950, 2890, 1601, 1460, 1370, 1180, 1030 cm$^{-1}$.

Elemental Analysis: C$_{41}$H$_{64}$SO$_7$. Theory %C, 70.25; %H, 9.20; %S, 4.57; %O, 15.98. Found: %C, 70.23, %H, 9.41; %S, 4.40; %O, 16.10.

EXAMPLE 4

3α,6α-di(2-tetrahydropyranyloxy)-25-cyano-5β-cholane (V)

A solution of 7.05 g (0.0101 mole) of the tosylate IV and 3.35 g (0.068 mole) of sodium cyanide in 250 ml anhydrous ethanol was heated at 79° C. under argon for 20 hr. After cooling at room temperature the amber solution was poured into 400 ml of ice water, stirred ½ hr, and the mixture extracted with heptane (5×100 ml). The combined heptane portions were dried (MgSO$_4$), heated with charcoal, filtered, and concentrated under reduced pressure to afford 2.0 g of white solid product, mp 154°–5° C.

The aqueous portion was then extracted with chloroform (2×50 ml), the chloroform layers combined, dried (MgSO$_4$), and evaporated to a yellow oil. This oil was dissolved in heptane, heated with charcoal, filtered, and concentrated to dryness under reduced pressure to afford an additional 2.5 g of white solid product, mp 152°–4° C. Total combined yield 74%.

NMR (CDCl$_3$): δ4.45–4.75 (br m, 2H, methine flanked by two oxygens), 3.15–4.15 (br m, 6H, adjacent to oxygen), 0.88 (s, 3H, C-19 —CH$_3$), 0.63 (s, 3H, C-18 —CH$_3$).

IR (CHCl$_3$): 2950, 2890, 2250, 1460, 1380, 1030 cm$^{-1}$.

Elemental Analysis: C$_{35}$H$_{57}$NO$_4$: Theory %C, 75.63; %H, 10.34; %N, 2.52; %O, 11.51. Found: %C, 75.53; %H, 10.45; %N, 2.48; %O, 11.36.

EXAMPLE 5

3α,6α-dihydroxy-25-cyano-5β-cholane (VI)

A solution of 2.15 g (0.00386 mole) of cyanide V and 0.21 g of p-toluenesulfonic acid in 45 ml H$_2$O and 130 ml ethanol was refluxed for 4 hr. The yellow solution was evaporated to dryness, affording an ivory solid. The solid was slurried in heptane and again evaporated to yield 1.39 g (93%) of fine white powder, mp 156°–58° C.).

NMR (CDCl$_3$): δ0.88 (s, 3H, C-19 —CH$_3$), 0.63 (s, 3H, C-18 —CH$_3$).

IR (CHCl$_3$): 3625, 3450, 2950, 2890, 2250, 1460, 1380, 1030 cm$^{-1}$.

Elemental Analysis: C$_{25}$H$_{41}$NO$_2$. Theory: %C, 77.47; %H, 10.66; %N, 3.61; %O, 8.26. Found: %C, 77.32; %H, 10.72; %N, 3.56; %O, 8.41.

EXAMPLE 6

3α,α6-dihydroxy-5β-homocholanic acid (VII)

A solution of 2.60 g (0.0067 mole) of the cyanide VI in 75 ml ethanol and 75 ml aqueous 1 N NaOH was refluxed 74 hr. The yellow solution was poured into 600 ml of water and the mixture adjusted to pH 3 by the addition of 5% HCl. The resulting precipitate was collected on a filter, washed extensively with water, and dried under vacuum. Total yield of the acid as a fine ivory powder was 2.56 g (94%), mp 197°–98° C.

Elemental Analysis: $C_{25}H_{42}O_4$. Theory: %C, 73.85; %H, 10.41; %O, 15.74. Found: %C, 74.02; %H, 10.51; %O, 15.42.

EXAMPLE 7

Methyl 3α,6α-dihydroxy-5β-homocholanate (VIII)

A solution of 2.40 g (0.0059 mole) of the acid VII and 0.4 g of p-toluenesulfonic acid in 400 ml of anhydrous ethanol was refluxed 48 hr using a Soxhlet extractor containing type 3A molecular sieves. The resulting yellow solution was evaporated to dryness and the light brown solid thus produced was heated in boiling heptane. A small amount of insoluble material was removed via filtration. The filtrate was concentrated under reduced pressure to half volume, and the solution cooled.

The resulting ivory solid was collected by filtration and dried under vacuum, and totalled 1.49 g (62%), mp 185°–87° C.

NMR (CDCl$_3$): δ3.63 (s, 3H, —OCH$_3$), 0.88 (s, 3H, C-19, —CH$_3$), 0.63 (s, 3H, 3-18 —CH$_3$).

IR (CHCl$_3$): 3640, 3460, 1735, 1460, 1380, 1205 cm$^{-1}$.

EXAMPLE 8

Methyl 3α,6α-di-p-toluenesulfonoxy-5β-homocholanate (IX)

To a solution of 1.5 g (0100356 mole) of the ester VIII in 75 ml of dry pyridine was added 1.7 g (0.0089 mole) of p-toluenesulfonyl chloride at room temperature, and the mixture stored at 3° C. for 24 hr.

The cold pyridine solution was then poured into 150 ml of ice water and the mixture adjusted to pH 3 by the addition of concentrated HCl. The resulting precipitate was collected by filtration, washed extensively with water, and dried under vacuum. The di-tosylate totalled 1.85 g (72%) of ivory powder, mp 61°–63° C.

NMR (CDCl$_3$): δ7.10–7.80 (ABq, 8H, aromatic), 3.63 (s, 3H, —OCH$_3$), 2.42 (s, 3H, Ar —CH$_3$), 0.83 (s, 3H, C-19 —CH$_3$), 0.60 (s, 3H, C-18 —CH$_3$).

IR (CHCl$_3$): 2960, 2890, 1735, 1601, 1460, 1365, 1190, 1180 cm$^{-1}$.

Elemental Analysis: %C, 65.90; %H, 7.74; %S, 8.80; %O, 17.56. Found: %C, 66.10; %H, 7.78; %S, 8.44; %O, 17.68.

EXAMPLE 9

Methyl 3β-acetoxy-5-homocholenate (X)

A solution of 1.45 g (0.0020 mole) of the ditosylate IX and 2.08 g (0.0212 mole) of potassium acetate in 22 ml dimethylformamide and 2 ml of water was heated at 105° C. for 5 hr. The hot reaction mixture was then poured into a cold 40 ml solution of 5% HCl. The tacky solid was collected filtration, washed extensively with water, and dried under vacuum. Total product collected: 0.60 g (67%) mp 48°–55° C.

IR (CHCl$_3$); 2960, 2890, 1730, 1440, 1380, 1205 cm$^{-1}$.

EXAMPLE 10

25-Hydroxycholesterol (XI)

A solution of 0.60 g (0.00135 mole) of the crude ester X in 44 ml of dry tetrahydrofuran was added dropwise under argon to a solution of 12 ml (0.0345 mole) of etherial methyl magnesium bromide in 50 ml of dry tetrahydrofuran, and stirred at room temperature for 24 hr. The reaction solution was then added dropwise to a solution of 10 g ammonium chloride in 60 ml of water. The entire mixture was evaporated to dryness, and the white solid residue slurried in chloroform. After removing the solid by filtration, the chloroform was concentrated to dryness and the resulting ivory powder dissolved in boiling heptane, filtered, and allowed to cool. The product was collected as a fine white powder, 0.32 g (60%), mp 169°–174° C.

NMR (CDCl$_3$): δ5.27–5.43 (m, 1H, vinyl), 1.22 (s, 6H, gem dimethyl), 1.00 (s, 3H, C-19 —CH$_3$), 0.68 (s, 3H, C-18 —CH$_3$).

IR (CHCl$_3$): 3640, 3450, 2950, 2890, 1470, 1380 cm$^{-1}$.

Elemental Analysis: $C_{27}H_{46}O_2$: Theory: %C 80.54; %H, 11.51; %O, 7.75. Found: %C, 80.50; %H, 11.48; %O, 8.02.

EXAMPLE 11

3α,6α-Dihydroxy-24-Cyano-5β-Cholane (VI) Synthesized with Methoxyethoxymethyl MEM Ether Protection To a solution of 4.06 g (0.01 mole) of methyl hyodeoxycholate in 40 ml of methylene chloride, 3.74 g of β-methoxyethoxymethyl chloride and 1.93 g of diisopropyl ethylamine were added. After 5 hr of stirring at room temperature, the reaction mixture was diluted with 40 ml of ether, washed with water, dried and the solvent evaporated. The residue, the 3α,6α-di-MEM ether of methyl hyodeoxycholate, was dissolved in toluene and added dropwise to an 80° C. solution of 1.2 g lithium aluminum hydride in toluene, under a nitrogen atmosphere. After an additional hr at 80° C., the reaction mixture was cooled and slowly mixed with aqueous alkali, maintaining the temperature below 20° C. The organic layer was separated, washed with water, dried, and the toluene evaporated. The residue was dissolved in pyridine, p-toluenesulfonyl chloride added with cooling and kept at 3° C. for 24 hr. Then, the mixture was poured into ice water and the resulting two-phase solution was extracted with warm heptane. The heptane extracts were combined, dried, and the solvent evaporated. The residue was dissolved in dimethylformamide, potassium cyanide was added and the reaction mixture was heated to approximately 100° C. for 20 hr. After cooling, the solution was poured into ice water, extracted with chloroform, the chloroform layer dried, and the solvent evaporated. The residue was dissolved in 60 ml of methylene chloride containing 0.9 ml of methanol, zinc bromide was added and the mixture stirred overnight. Ether was added, the solution washed with water, the organic layer dried and the solvent evaporated. The residue was dissolved by warming in heptane, decolorized with charcoal, and the solution chilled. Fine white powder, mp 156°–158° C., was obtained, which was identical with the 3α,6α-dihydroxy-25-cyano-5β-cholane, obtained in Example 5.

EXAMPLE 12

3α,6α-25-Trihydroxy-5β-cholestane (XII)

A solution of 0.001 mole of methyl 3α,6α-diacetoxy-5β-homocholanate in 40 ml of tetrahydrofuran was added dropwise and under nitrogen to a solution of 0.04 mole of methyl magnesium bromide in 50 ml of tetrahydrofuran, and the mixture was stirred for 24 hr at room temperature. Then it was added dropwise to an aqueous ammonium chloride solution, the entire mixture evaporated to dryness, and the residue extracted with chloroform. The filtered chloroform extract was evaporated to dryness and the residue oxidized according to the Oppenauer method, as described in Example 13.

EXAMPLE 13

25-Hydroxy-5-Cholestane-3,6-dione 3,6-25-Dihydroxy-5-cholestane, the chloroform evaporation residue obtained in Example 12 was dissolved in toluene, cyclohexanone and aluminum isopropoxide were added, and the solution refluxed for 1 hr. The solvents were evaporated under reduced pressure, the residue dissolved in 95% ethanol and crystallized. The product was identical with the 25-hydroxy-5-cholestan-3,6-dione reported by T. A. Narwid et al., Helv. Chim. Acta, 57, 781 (1974).

While only certain embodiments and certain variations of my invention have been described in detail, it will be apparent to those skilled in this art that other embodiments may be practiced, and that many changes may be made all within the spirit of the invention, and all such embodiments and changes are considered to be embraced by and included within the scope of the appended claims.

What is claimed:

1. A steroid compound having the structure:

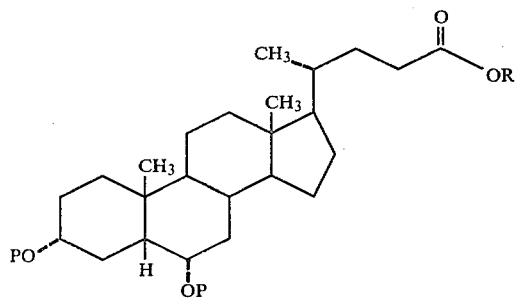

where P is alkyl, alkyl ether or 2-tetrahydropyranyl and R is alkyl.

2. A compound as set forth in claim 1 in which P is 2-tetrahydropyranyl.

3. A compound as set forth in claim 1 in which P is β-methoxyethoxymethyl.

4. A sterol compound having the structure:

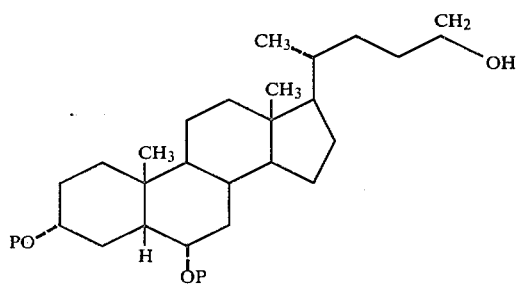

where P is alkyl, alkyl ether or 2-tetrahydropyranyl.

5. A sterol ether as set forth in claim 4 where P is β-methoxyethoxymethyl.

6. A compound having the structure:

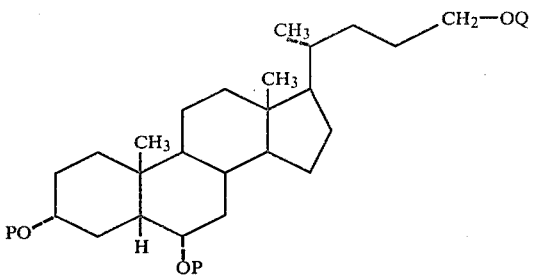

where P is alkyl, alkyl ether or 2-tetrahydropyranyl and Q is an aromatic sulfonyl group or an alkyl sulfonyl group.

7. A compound as set forth in claim 6 in which Q is p-toluenesulfonyl and P is 2-tetrahydropyranyl or β-methoxyethoxymethyl.

8. A sterol having the structure:

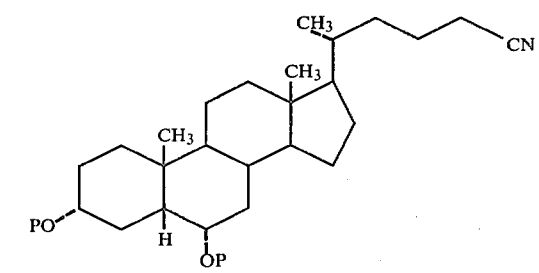

where P is alkyl, alkyl ether or tetrahydropyranyl.

9. A compound as set forth in claim 8 in which P is β-methoxyethoxymethyl.

10. A sterol compound having the structure:

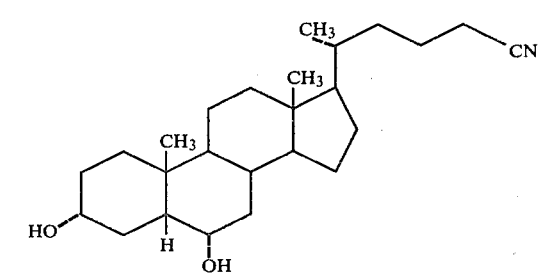

11. A sterol having the structure:

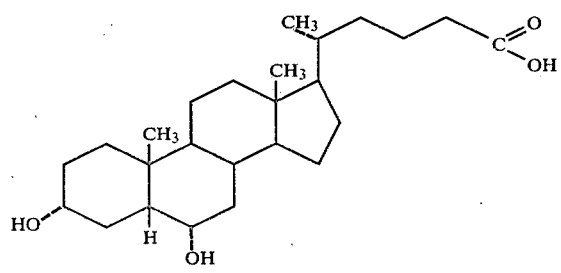

12. A sterol compound having the structure:

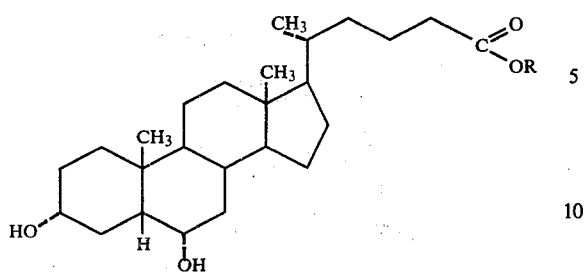

where R is an alkyl group having one to nine carbons.

13. A sterol compound having the structure:

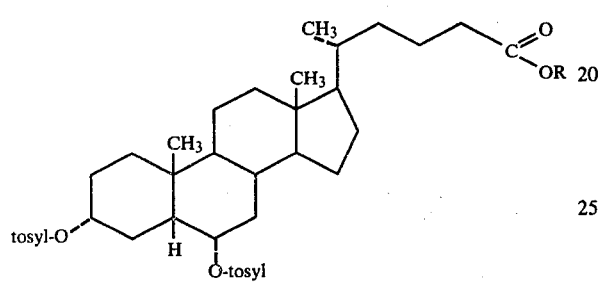

where R is an alkyl group having one to nine carbons.

14. A sterol compound having the structure:

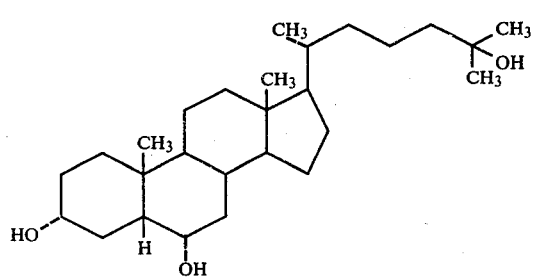

15. In a process for preparing a sterol compound the step of heating an ester of hydrodeoxycholic acid having the structure:

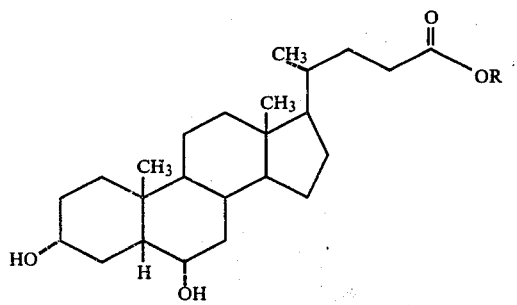

Where R is alkyl, in dioxane solution with dihydropyran in
the presence of p-toluenesulfonic acid or mixed with β-methoxyethoxymethyl chloride in methylene chloride solution in the presence of a tertiary amine to obtain the compound having the structure:

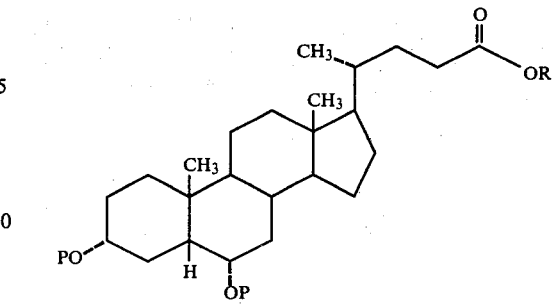

where P is 2-tetrahydropyranyl or β-methoxyethoxymethyl and R is alkyl.

16. In a process for preparing a sterol compound the step of heating a compound having the structure:

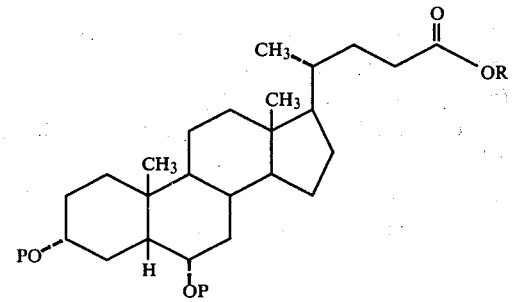

where P is 2-tetrahydropyranyl or β-methoxyethoxymethyl, in toluene solution with an alkaline reducing agent, to prepare a compound having the structure:

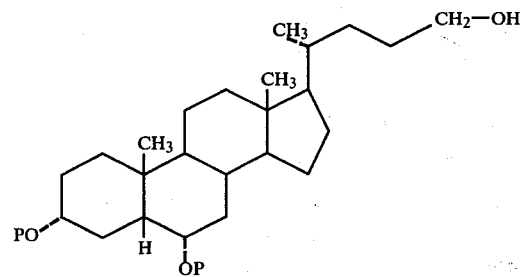

where P is 2-tetrahydropyranyl or β-methoxyethoxymethyl.

17. A process as set forth in claim 16 in which said alkaline reducing agent is a sodium, potassium or lithium complex of aluminum halide.

18. In a process for preparing a sterol compound, the step of mixing a compound having the structure:

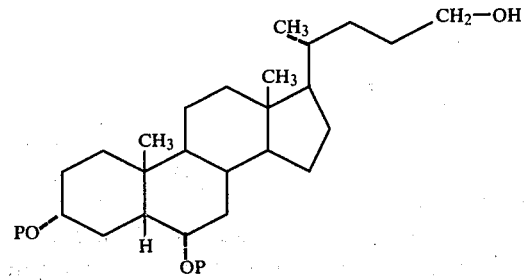

where P is 2-tetrahydropyranyl or β-methoxyethoxymethyl, in pyridine solution with an aromatic or alkyl sulfonyl chloride to obtain a compound having the structure:

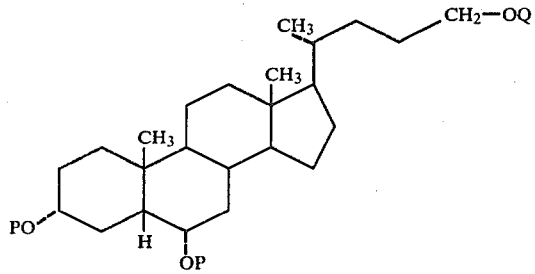

where P is 2-tetrahydropyranyl or β-methoxyethoxymethyl and Q is an aromatic or alkyl sulfonyl group.

19. A process as set forth in claim 18 in which said aromatic sulfonyl chloride is p-toluenesulfonyl chloride and Q is p-toluenesulfonyl.

20. In a process for preparing a sterol compound the step of treating a compound having the structure:

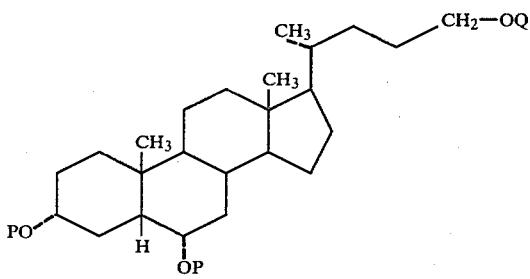

where P is 2-tetrahydropyranyl or β-methoxyethoxymethyl and Q is p-toluenesulfonyl with a potassium, sodium or lithium cyanide salt is dimethylformamide or in ethanol until the reaction takes place to form a sterol compound having the structure:

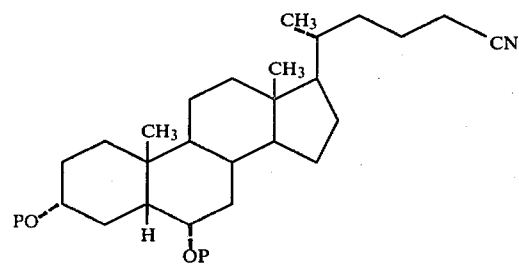

where P is 2-tetrahydropyranyl or β-methoxyethoxymethyl.

21. In a process for preparing a sterol compound the step of heating a sterol compound having the structure:

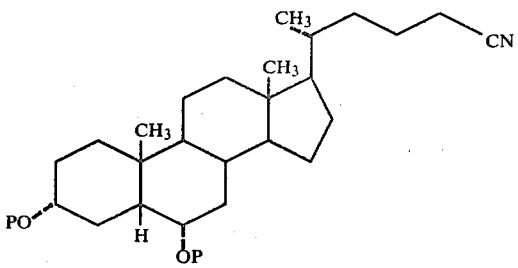

where P is 2-tetrahydropyranyl, in aqueous alcohol with p-toluenesulfonic acid to obtain a compound having the structure:

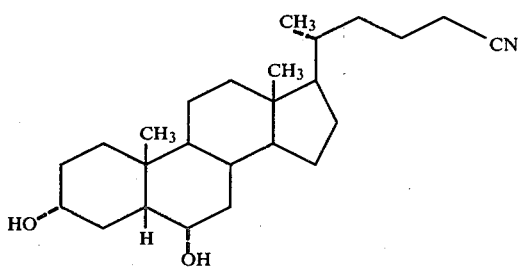

22. In a process for preparing a sterol having the structure:

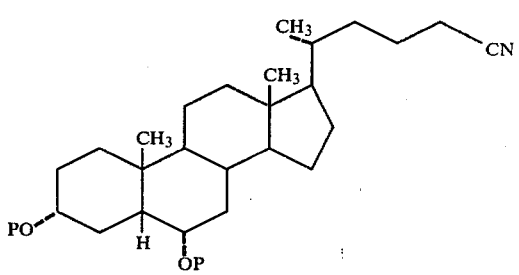

where P is β-methoxyethoxymethyl, the step of stirring the sterol so prepared with zinc bromide in a methylene chloride solvent containing a lower alkyl alcohol in an amount of 0.1 to 5%, the alcohol containing one to six carbons, to obtain a sterol having the structure:

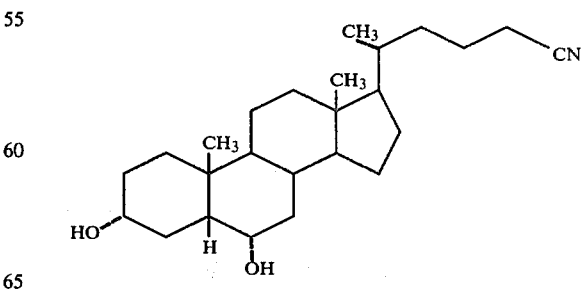

23. In a process for preparing a sterol, the step of saponifying a compound having the structure:

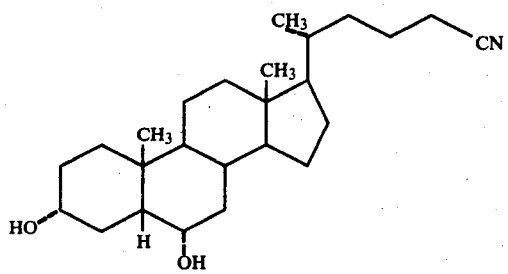

in aqueous alcohol with sodium hydorxide, and acidifying the resulting solution to obtain a sterol having the structure:

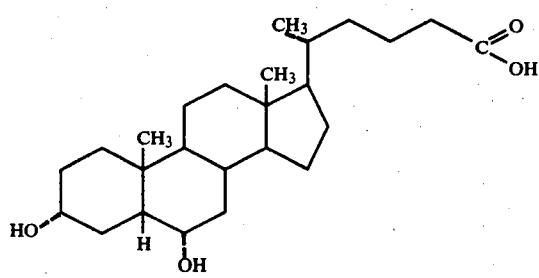

24. In a process for preparing a steroid compound, the step of heating a compound having the structure:

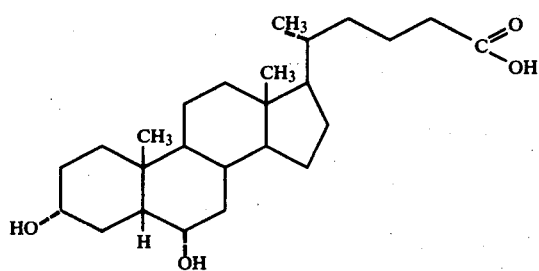

with p-toluenesulfonic acid in a lower alkyl alcohol solution, the alkyl alcohol containing one to nine carbons, to obtain a compound having the structure:

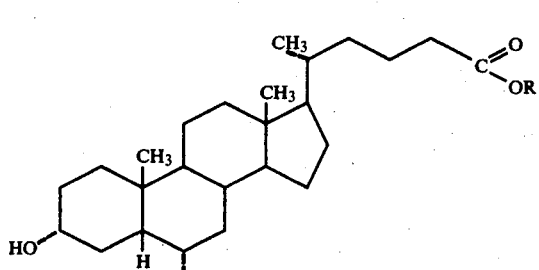

where R is a lower alkyl alcohol containing one to nine carbons.

25. In a process for preparing a steroid compound the step of mixing the compound

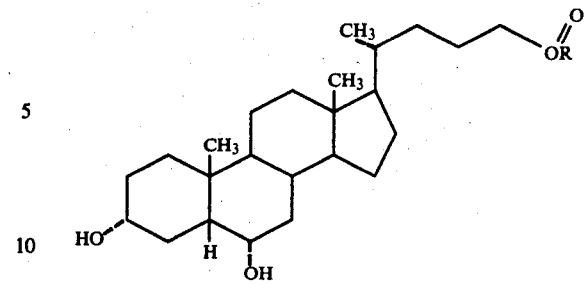

with methyl magnesium bromide in tetrahydrofuran solution to obtain the compound having the structure:

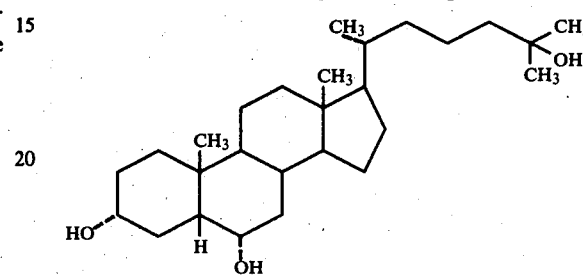

26. In a process for preparing a steroid compound the step of dissolving in pyridine the compound having the structure:

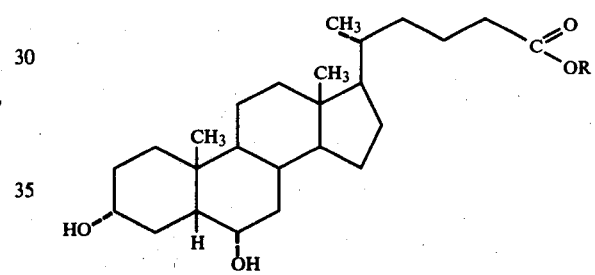

mixing a pyridine solution of said compound with p-toluenesulfonyl chloride to obtain the compound having the structure:

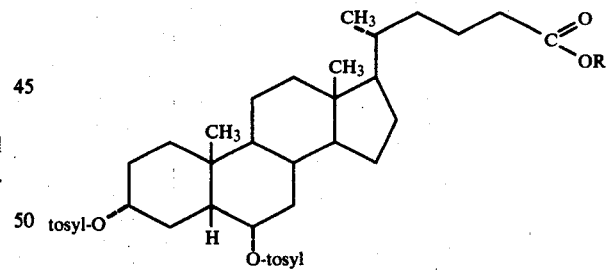

dissolving said compound in dimethylformamide, adding an aqueous solution of potassium acetate and heating the mixture of 90°–110° C. until both tosyloxy groups react, to obtain the compound having the structure:

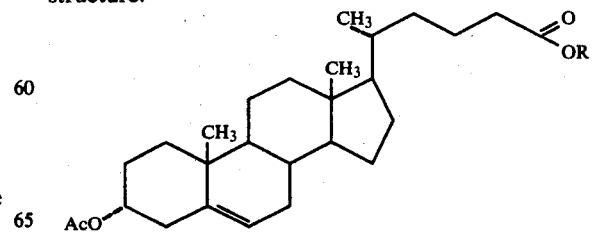

where R is a lower alkyl group having one to nine carbons.

* * * * *

UNITED STATES PATENT AND TRADEMARK OFFICE
CERTIFICATE OF CORRECTION

PATENT NO. : 4,217,279
DATED : August 12, 1980
INVENTOR(S) : Emil T. Kaiser

It is certified that error appears in the above—identified patent and that said Letters Patent is hereby corrected as shown below:

Columns 5 thru 8 should be deleted to insert the attached columns 5 thru 8, respectively, therefor. (This correction applys to the grant exclusively)

Claim 15, line 2, "hydrodeoxycholic acid" should be --hyodeoxycholic acid--.

Claim 20, line 6, "cyanide salt is dimethylformamide" should be --cyanide salt in dimethylformamide--.

Claim 23, column 17, line 4, "hydorxide" should be --hydroxide--

Claim 26, column 18, in the last structural formula of the claim at line 65, AcO is connected to the ring structure by a dotted line, but should be connected to the ring structure by a solid line as follows:

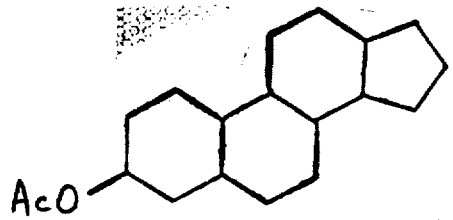

Signed and Sealed this

Second Day of December 1980

[SEAL]

Attest:

SIDNEY A. DIAMOND

Attesting Officer

Commissioner of Patents and Trademark

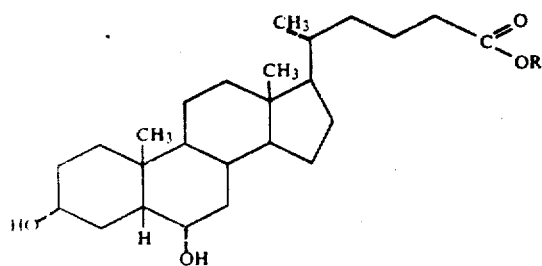

Compound VIII where R is a lower alkyl group containing one to nine carbons.

Compound VIII can be utilized in a variety of ways in the synthesis of hydroxylated cholesterols as illustrated by following synthetic pathways.

According to one of the pathways Compound VIII may be mixed at room temperature in pyridine solution with p-toluenesulfonyl chloride and the mixture stored at lower temperatures and for longer periods of time, for example, for 24 hr at 3° C. From this mixture an ester, preferably the methyl ester of 3α,6α-di-p-toluenesulfonyloxy-5β-homocholanic acid, may be isolated, herein designated Compound IX, having the structure:

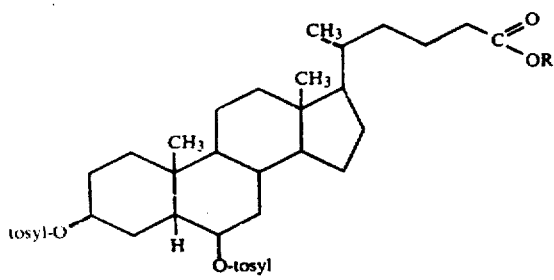

Compound IX where R is a lower alkyl group having one to nine carbons.

Compound IX may be dissolved in dimethylformamide, potassium acetate in aqueous solution is added, and the mixture heated to 90° C. to 110° C. for several hours, for example 5 hrs. From the mixture a compound may be isolated, herein designated Compound X, having the structure:

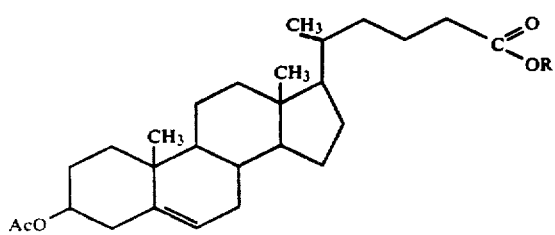

Compound X where R is a lower alkyl group having one to nine carbons.

Compound X has been described by J. C. Babcock and J. A. Campbell in U.S. Pat. No. 3,833,622 (1974). According to Example 4 of Babcock, a conjugated 7,8-double bond may be introduced into Compound X, which, in this Example, is called 3β-hydroxy-25-homochol-5-enate, 3-acetate, and designated Compound VII by Babcock. The resulting methyl 3β-hydroxy-25-homochol-5,7-dienate 3-acetate is disclosed to be transformed by several synthetic steps and by irradiation into 25-hydroxycholecalciferol.

It is a substantial advantage that in my invention compound X may be produced from an available raw material, hog bile, while Babcock obtains this compound from a minor oxidation product of cholesterol, which is difficult to prepare and in short supply.

Compound X, according to the process of my invention, may be dissolved in tetrahydrofuran, methyl magnesium bromide in tetrahydrofuran solution added, and the mixture stirred for a prolonged period, for example 24 hours. From the reaction mixture 25-hydroxycholesterol, herein designated Compound XI, may be isolated, having the structure:

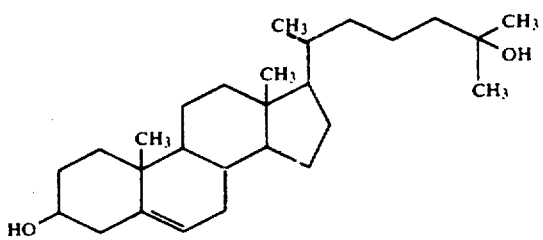

Compound XI

Compound XI may be transformed by an 8 step process into 1,25-dihydroxycholecalciferol according to D. H. R. Barton, R. H. Hesse, M. M. Pechet and E. Rizzardo, J.C.S. Chem. Commun., 203, 1974.

In another sequence of reactions Compound VIII may be dissolved in tetrahydrofuran and the solution added dropwise to a solution of methyl magnesium bromide in tetrahydrofuran. The mixture may be stirred at room temperature for a longer period, for example 24 hours, and magnesium complex decomposed with aqueous ammonium chloride and 3α,6α-dihydroxy-5β-chloestane isolated, herein designated as Compound XII, having the structure:

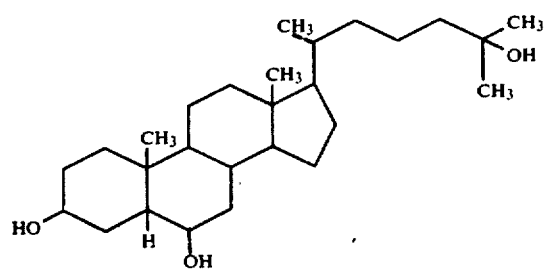

Compound XII

Compound XII may be dissolved in toluene, and after the addition of cyclohexanone and aluminum isopropoxide, the solution may be refluxed for 1 to 2 hours. After the solvents are evaporated from the residue, 25-hydroxy-5α-cholestan-3,6-dione is isolated. This is a compound described by T. A. Narwid, J. F. Blount, J. A. Iacobelli and M. R. Uskokovic in Helv. Chim. Acta, 57, 781 (1974). These authors converted 25-hydroxy- 5α-cholestane-3,6-dione into 1α,25-dihydroxycholesterol, used for the production of 1α,25-dihydroxycholecalciferol.

Specific examples for carrying out my improved synthesis are given as follows:

EXAMPLE 1

Methyl 3α,6α-Di(2-tetrahydropyranyloxy)-5β-cholanate (II)

To a solution of 100.0 g (0.2557 mole) of methyl hyodeoxycholate and 5.68 g of p-toluenesulfonic acid in 2000 ml of p-dioxane was added 153.7 g (1.62 mole, 148.6 ml) of dihydropyran over a period of 30 min under argon atmosphere. After stirring overnight at room temperature, the pH of the solution was adjusted to approximately pH 8 by the addition of 55 ml of 50/50 methanol/29% ammonium hydroxide. The solution was concentrated to a yellow oil under reduced pressure and the residue stirred in heptane 4 hr, then filtered to remove the precipitated p-toluenesulfonic acid. The filtrate was heated with charcoal, filtered, and evaporated to yield 116.8 g (80%) of the di-tetrahydropyranyl ether as a colorless viscous oil.

NMR (CDCl$_3$): δ4.50-4.80 (br m, 2H, methine flanked by two oxygens), 3.30-4.15 (br m, 6H, adjacent to oxygen), 3.63 (s, 3H, —OCH$_3$), 0.88 (s, 3H, C-19 —CH$_3$), 0.63 (s, 3H, C-18 —CH$_3$).

IR (CHCl$_3$): 2950, 2890, 1740, 1460, 1380, 1030 cm$^{-1}$.

Elemental Analysis: C$_{35}$H$_{58}$O$_6$: Theory %C 73.13; %H 10.17, %O 16.70. Found: %C 73.36, %H 10.02; %O 16.76.

EXAMPLE 2

3α,6α-Di(2-tetrahydropyranyloxy)-24-hydroxy-5β-cholane (III)

To an 80° C. solution of 56 ml (0.202 mole) of Vitride T reagent [sodium bis(2-methoxyethoxy)aluminum hydride] in 500 ml dry toluene under argon atmosphere was added dropwise a solution of 44 g (0.0765 mole) of methyl 3α,6α-di(2-tetrahydropyranyloxy)-5β-cholanate in 75 ml dry toluene. After an additional hr at 80° C. the yellow solution was allowed to cool at room temperature, then added dropwise to 400 ml of 20% NaOH over a period of one hr with the temperature maintained below 20° C.

After stirring an additional hr, the layers were separated and the aqueous layer washed with 3×100 ml of toluene. The organic layers were combined, dried (MgSO$_4$) and concentrated under reduced pressure resulting in a yellow oil which was heated in heptane, treated with charcoal, filtered, and concentrated to yield 40.72 g (97%) of the alcohol as a colorless oil.

NMR (CDCl$_3$): δ4.45-4.75 (br m, 2H, methine flaked by two oxygens), 3.20-4.10 (br m, 9H adjacent to oxygen), 0.88 (s, 3H, C-19 —CH$_3$), 0.62 (s, 3H, C-18 —CH$_3$).

IR (CHCl$_3$): 3500, 2950, 2890, 1460, 1360, 1030 cm$^{-1}$.

EXAMPLE 3

3α,6α-di(2-tetrahydropyranyloxy)-24-p-toluenesulfonoxy-5β-cholane (IV)

To a solution of 7.10 g (0.013 mole) of the alcohol III in 200 ml of dry pyridine was added 4.19 g (0.022 mole) of p-toluenesulfonyl chloride at room temperature. The reaction mixture was chilled at 3° C. for 23 hr, then poured into 200 ml of ice water with stirring. The resulting two phase mixture was extracted with warm heptane (4×30 ml), the heptane portion dried (MgSO$_4$), heated with charcoal, filtered and concentrated under reduced pressure. The resulting colorless viscous oil totalled 7.05 g (77%).

NMR (CDCl$_3$): δ7.10-7.80 (ABq, 4H, aromatic), 4.50-4.75 (br m, 2H, methine flanked by two oxygens), 3.20-4.10 (br m, 8H adjacent to oxygen), 2.42 (s, 3H Ar-CH$_3$), 0.88 (s, 3H, C-19 —CH$_3$), 0.57 (s, 3H, C-18 —CH$_3$).

IR (CHCl$_3$): 2950, 2890, 1601, 1460, 1370, 1180, 1030 cm$^{-1}$.

Elemental Analysis: C$_{41}$H$_{64}$SO$_7$: Theory %C, 70.25, %H, 9.20; %S, 4.57; %O, 15.98. Found: %C, 70.23, %H, 9.41; %S, 4.40; %O, 16.10.

EXAMPLE 4

3α,6α-di(2-tetrahydropyranyloxy)-25-cyano-5β-cholane (V)

A solution of 7.05 g (0.0101 mole) of the tosylate IV and 3.35 g (0.068 mole) of sodium cyanide in 250 ml anhydrous ethanol was heated at 79° C. under argon for 20 hr. After cooling at room temperature the amber solution was poured into 400 ml of ice water, stirred ½ hr, and the mixture extracted with heptane (5×100 ml). The combined heptane portions were dried (MgSO$_4$), heated with charcoal, filtered, and concentrated under reduced pressure to afford 2.0 g of white solid product, mp 154°-5° C.

The aqueous portion was then extracted with chloroform (2×50 ml), the chloroform layers combined, dried (MgSO$_4$), and evaporated to a yellow oil. This oil was dissolved in heptane, heated with charcoal, filtered, and concentrated to dryness under reduced pressure to afford an additional 2.5 g of white solid product, mp 152°-4° C. Total combined yield 74%.

NMR (CDCl$_3$): δ4.45-4.75 (br m, 2H, methine flanked by two oxygens), 3.15-4.15 (br m, 6H, adjacent to oxygen), 0.88 (s, 3H, C-19 —CH$_3$), 0.63 (s, 3H, C-18 —CH$_3$).

IR (CHCl$_3$): 2950, 2890, 2250, 1460, 1380, 1030 cm$^{-1}$.

Elemental Analysis: C$_{35}$H$_{57}$NO$_4$: Theory %C, 75.63; %H, 10.34; %N, 2.52; %O, 11.51. Found: %C, 75.53; %H, 10.45; %N, 2.48; %O, 11.36.

EXAMPLE 5

3α,6α-dihydroxy-25-cyano-5β-cholane (VI)

A solution of 2.15 g (0.00386 mole) of cyanide V and 0.21 g of p-toluenesulfonic acid in 45 ml H$_2$O and 130 ml ethanol was refluxed for 4 hr. The yellow solution was evaporated to dryness, affording an ivory solid. The solid was slurried in heptane and again evaporated to yield 1.39 g (93%) of fine white powder, mp 156°-58° C.

NMR (CDCl$_3$): δ0.88 (s, 3H, C-19 —CH$_3$), 0.63 (s, 3H, C-18 —CH$_3$).

IR (CHCl$_3$): 3625, 3450, 2950, 2890, 2250, 1460, 1380, 1030 cm$^{-1}$.

Elemental Analysis: C$_{25}$H$_{41}$NO$_2$. Theory: %C, 77.47; %H, 10.66; %N, 3.61; %O, 8.26. Found: %C, 77.32; %H, 10.72; %N, 3.56; %O, 8.41.

EXAMPLE 6

3α,α6-dihydroxy-5β-homocholanic acid (VII)

A solution of 2.60 g (0.0067 mole) of the cyanide VI in 75 ml ethanol and 75 ml aqueous 1 N NaOH was refluxed 74 hr. The yellow solution was poured into 600